U.S. Patent [19]  [11] 3,933,922
Mark  [45] Jan. 20, 1976

[54] SUBSTITUTED POLYHALOGENATED CYCLOPENTADIENES

[75] Inventor: Victor Mark, Ransomville, N.Y.

[73] Assignee: Monsanto Company, St. Louis, Mo.

[22] Filed: Dec. 6, 1973

[21] Appl. No.: 422,246

Related U.S. Application Data

[60] Division of Ser. No. 135,391, April 19, 1971, Pat. No. 3,799,994, Continuation-in-part of Ser. No. 786,429, Dec. 23, 1968, abandoned, which is a continuation-in-part of Ser. No. 44,890, July 25, 1960, Pat. No. 3,478,117.

[52] U.S. Cl............................................. 260/611 R
[51] Int. Cl.² ....................................... C07C 43/18
[58] Field of Search ............................... 260/611 R

[56] References Cited
UNITED STATES PATENTS

| | | | |
|---|---|---|---|
| 2,806,049 | 9/1957 | Raab et al. | 260/461 |
| 3,037,044 | 5/1962 | Bruson et al. | 260/461 |
| 3,270,066 | 8/1966 | von Brachel | 260/648 C |
| 3,478,117 | 11/1969 | Mark | 260/648 |

*Primary Examiner*—Bernard Helfin
*Attorney, Agent, or Firm*—Richard H. Shear

[57] ABSTRACT

Compounds of the formula

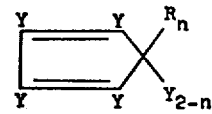

wherein Y is independently selected from the group consisting of methyl, hydrogen and a halogen of atomic weight between 35 and 80 with at least four of the Y substituents being said halogen; each R is independently selected from the group consisting of alkyl having at least one and a maximum of 12 carbon atoms, alkenyl having at least 2 and a maximum of 5 carbon atoms, alkoxyalkyl having at least 2 and a maximum of 6 carbon atoms and cycloalkyl having at least 5 and a maximum of 6 carbon atoms, and $n$ is one of the integers one or two.

These compounds possess insecticidal activity and are valuable intermediates for the preparation of insecticides having low mammalian toxicity.

3 Claims, No Drawings

SUBSTITUTED POLYHALOGENATED CYCLOPENTADIENES

This is a division, of application Ser. No. 135,391, filed Apr. 19, 1971 now U.S. Pat. No. 3,799,994 which in turn is a continuation-in-part of application Ser. No. 786,429, filed Dec. 23, 1968 and now abandoned, which in turn is a continuation-in-part of application Ser. No. 44,890, filed July 25, 1960, now issued as U.S. Pat. No. 3,478,117.

This invention relates to novel substituted polyhalogenated cyclopentadienes which possess insecticidal properties and which are valuable intermediates for the preparation of insecticides having low mammalian toxicity.

The compounds of the present invention are of the formula

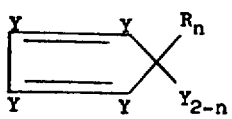

wherein Y is independently selected from the group consisting of methyl, hydrogen and a halogen of atomic weight between 35 and 80 with at least four of the Y substituents being said halogen; each R is independently selected from the group consisting of alkyl having at least 1 and a maximum of 12 carbon atoms, alkenyl having at least 2 and a maximum of 5 carbon atoms, alkoxyalkyl having at least 2 and a maximum of 6 carbon atoms and cycloalkyl having at least 5 and a maximum of 6 carbon atoms, and $n$ is one of the integers 1 or 2.

In a preferred embodiment of this invention Y is chlorine or bromine; R is selected from the group consisting of alkyl having at least 1 and a maximum of 8 carbon atoms; alkenyl having at least 3 and a maximum of 5 carbon atoms, alkoxyalkyl having at least 2 and a maximum of 4 carbon atoms, cycloalkyl having at least 5 and a maximum of 6 carbon atoms; and $n$ is 1.

The preparation of the compounds of this invention, illustrated in the following examples, is fully discussed in my earlier application Ser. No. 44,890, filed July 25, 1960, now U.S. Pat. No. 3,478,117. The preparation of the starting polyhalogenated cyclopentadienes and the phosphorous acid esters are by known methods.

EXAMPLE 1

Preparation of 1,2,3,4,5-pentachloro-5-ethylcyclopentadiene

A solution of 272.8 g. (1.0 mole) of hexachlorocyclopentadiene in 300 ml. of petroleum ether (pentane range) was charged to a 2 liter 3 neck flask equipped with stirrer, thermometer, dropping funnel and an exit line protected with a drying tube. The flask was immersed in ice-water and triethyl phosphite (182.8 g., 1.1 mole) was added slowly from the dropping funnel at such a rate that the temperature of the reaction mixture did not exceed +15°C. After the addition was completed (which required 5 hours) the clear, brown solution was, after the stripping of the solvent, fractionated in vacuum through a 20 inch column, filled with glass helices. A lower boiling fraction, 161 g., b.p. 39°C. at 0.4 mm., $n_D^{25}$ 1.4253 consisted of pure ethyl phosphorochloridate, Cl(EtO)$_2$PO, which, accordingly, was obtained in 93.4% yield. Then the temperature rose fast in the column and a pale yellow oil distilled over sharply at 50°C. and 0.18 mm. Infrared and elemental analyses indicated that the yellow oil, $n_D^{25}$ 1.5394, is pure 1,2,3,4,5-pentachloro-5-ethylcyclopentadiene.

Analysis for C$_7$H$_5$Cl$_5$: Calculated: C, 31.56%; H, 1.89%; Cl, 66.55%. Found: C, 31.49%; H, 1.91%; Cl, 66.69%.

EXAMPLE 2

1,2,3,4,5-pentachloro-5-ethylcyclopentadiene

A solution of triethyl phosphite (182.8 g., 1.1 mole) in 200 ml. of petroleum ether (pentane range) was charged to the equipment of the preceding example, which was immersed into a rock-salt-ice mixture. When the temperature of the solution reached 0°C. hexachlorocyclopentadiene (272.8 g., 1.0 mole), dissolved in 100 ml. of light petroleum ether, was added slowly to the well stirred solution at such a rate that the temperature of the mixture did not exceed +5°C. The addition required 10 hours. The clear, brown solution was poured with good stirring into a 5 liter 3 neck flask containing 2 liters of water and, after 1 hour of stirring, the product was steam distilled. After the separation of the low boiling petroleum ether 1,2,3,4,5-pentachloro-5-ethyl-cyclopentadiene, completely free of any phosphorus compound, distilled over as a pale yellow heavy oil, $n_D^{25}$ 1.5398, the infrared spectrum of which matched perfectly that of the previous example. The product weighed 257.0 g., which corresponds to a 96.4% yield.

EXAMPLE 3

1,2,3,4,5-pentachloro-5-isopropylcyclopentadiene

Substituting triisopropyl phosphite (208.2 g., 1.0 mole) for triethyl phosphite but maintaining otherwise identical conditions with those of Example 1 resulted in the formation of isopropyl phosphorochloridate, Cl(i-so-PrO)$_2$PO (b.p. 48°C. at 0.55 mm., $n_D^{25}$ 1.4198, 197 g. or 98.5% yield) and of 1,2,3,4,5-pentachloro-5-isopropylcyclopentadiene, which had b.p. 67.5°C. at 0.42 mm., $n_D^{25}$ 1.5397 and which was obtained in 96% yield (269.0 g.).

Analysis for C$_8$H$_7$Cl$_5$: Calculated: C, 34.26%; H, 2.52%; Cl, 63.22%. Found: C, 33.78%; H, 2.80%; Cl, 63.53%.

EXAMPLE 4

1,2,3,4,5-pentachloro-5-methylcyclopentadiene

When trimethyl phosphite, 175.7 g. (1.4 mole), was substituted for triethyl phosphite in the procedure described in Example 2 and the reaction was carried out at around 20°C. 224.0 g. of 1,2,3,4,5-pentachloro-5-methylcyclopentadiene was isolated by distillation between 42.5 and 44.0°C. at 0.27 mm.; $n_D^{25}$ 1.5460, in 89% yield.

Analysis for C$_6$H$_3$Cl$_5$: Calculated: C, 28.56%; H, 1.19%; Cl, 70.25%. Found: C, 28.06%; H, 1.26%; Cl, 69.08%.

When the workup of the reaction mixture was carried out by fractionation instead of hydrolysis, 140.0 g. (97%) of methyl phosphorochloridate, Cl(CH$_3$O)$_2$PO, (b.p. 75°C. at 15 mm. $n_D^{25}$ 1.4194) was isolated in addition to the alkylated product.

EXAMPLE 5

5-n-butyl-1,2,3,4,5-pentachlorocyclopentadiene

The replacement of triethyl phosphite with tri-n-butyl phosphite (250.3 g., 1.0 mole) in Example 1 resulted in the formation of 5-n-butyl-1,2,3,4,5-pentachlorocyclopentadiene, b.p. 72.5°C. at 0.28 mm., $n_D^{25}$ 1.5270 in 84% yield.

Analysis for $C_9H_9Cl_5$: Calculated: C, 36.71%; H, 3.08%; Cl, 60.21%. Found: C, 36.24%, H, 3.08%; Cl, 60.20%.

EXAMPLE 6

1,2,3,4,5-pentachloro-5-(2-ethylhexyl)cyclopentadiene

The substitution of tris(2-ethylhexyl) phosphite (418.6 g., 1.0 mole) for triethyl phosphite in Example 1 resulted in the formation of 1,2,3,4,5-pentachloro-5-(2-ethylhexyl)cyclopentadiene, which boiled between 106° and 107°C. at 0.31 mm., $n_D^{25}$ 1.5172 and which was obtained in 91% yield (320 g.).

Analysis for $C_{13}H_{17}Cl_5$: Calculated: C, 44.53%; H, 4.90%; Cl, 50.57%. Found: C, 43.72%; H, 4.83%; Cl, 50.50%.

EXAMPLE 7

1,2,3,4,5-pentachloro-5-cyclohexylcyclopentadiene

When triethyl phosphite of Example 2 was replaced with the equivalent amount of tricyclohexyl phosphite and the reaction was carried out between 17° and 35°C. 1,2,3,4,5-pentachloro-5-cyclohexylcyclopentadiene was isolated by distillation between 95° and 98°C. at 0.15 mm.; $n_D^{25}$ 1.5564.

Analysis for $C_{11}H_{11}Cl_5$: Calculated: C, 41.22%; H, 3.46%; Cl, 55.32%. Found: C, 41.40%; H, 3.45%; Cl, 54.39%.

EXAMPLE 8

5-allyl-1,2,3,4,5-pentachlorocyclopentadiene

Carrying out the procedure of Example 2 between 4° and 25°C. and replacing triethyl phosphite with triallyl phosphite (280 g., 1.39 mole) resulted in the formation of 211 g. (0.76 mole 76% yield) of 5-allyl-1,2,3,4,5-pentachlorocyclopentadiene, b.p. 63°C. at 0.48 mm., $n_d^{25}$ 1.5450.

Analysis for $C_8H_5Cl_5$: Calculated: C, 34.51%; H, 1.81%; Cl, 63.68%. Found: C, 34.41%; H, 2.01%; Cl, 63.23%.

When the workup of the reaction mixture was carried out by fractionation instead of steam distillation, allyl phosphorochloridate was obtained as a colorless liquid, b.p. 49°C. at 0.27 mm., $n_D^{21}$ 1.4410.

EXAMPLE 9

1,2,3,4,5-pentachloro-5-(2-methoxyethyl)cyclopentadiene

The replacement of triethyl phosphite was tris-(2-methoxyethyl) phosphite (307.2 g., 1.2 mole) in Example 2 and the raising of the reaction temperature to 25°-43°C. resulted in the formation of 1,2,3,4,5-pentachloro-5-(2-methoxyethyl)cyclopentadiene, b.p. 71°C. at 0.22 mm., $n_D^{25}$ 1.5326.

Analysis for $C_8H_7Cl_5O$: Calculated: C, 32.41%; H, 2.38%; Cl, 59.81%. Found: C, 31.34%; H, 2.56%; Cl, 60.49%.

EXAMPLE 10

1,2,3,4,5-pentachloro-5-ethylcyclopentadiene via phosphonites

When diethyl phenylphosphonite (200.0 g., 1.1 mole) was substituted for triethyl phosphite in the procedure of Example 1 a substantial yield of 1,2,3,4,5-pentachloro-5-ethylcyclopentadiene was obtained, the infrared spectrum of which matched perfectly that of Example 1.

EXAMPLE 11

1,2,3,4,5-pentachloro-5-ethylcyclopentadiene via phosphinites

When ethyl diphenylphosphinite (232 g., 1.0 mole) was substituted for triethyl phosphite and the reaction temperature was raised to 25° to 40°C. in the procedure of Example 1 a substantial yield of 1,2,3,4,5-pentachloro-5-ethylcyclopentadiene was obtained, identical in every respect with the product of Example 1.

EXAMPLE 12

1,2,3,4,5-pentabromo-5-ethylcyclopentadiene

The procedure of Example 1 was duplicated except that hexabromocyclopentadiene (539.6 g., 1.0 mole) was used in place of hexachlorocyclopentadiene and hexane (2.5 l.) was used in place of petroleum ether. A 93% yield of 1,2,3,4,5-pentabromo-5-ethylphosphite was obtained as a heavy oil $n_D^{25}$ 1.6423, which decomposes above 130°C. Isolated was also, through fractionation, ethyl phosphorobromidate, $Br(C_2H_5O)_2PO$, b.p. 58°-59°C. at 0.25 mm., $n_D^{25}$ 1.4443, in better than 78% yield.

EXAMPLE 13

Tetrachloroethylcyclopentadienes

The replacement of hexachlorocyclopentadiene with 1,2,3,4,5-pentachlorocyclopentadiene (238.4 g., 1.0 mole) in the procedure of Example 1 while raising the temperature to 22° to 52°C. yielded a mixture of 3 isomeric components identified as 1,2,4,5-tetrachloro-5-ethylcyclopentadiene, 1,2,3,5-tetrachloro-5-ethylcyclopentadiene, 1,2,3,4-tetrachloro-5-ethylcyclopentadiene, b.p. 49°-52°C. at 0.22 mm., $n_D^{25}$ 1.5325 in better than 80% yield.

Analysis for $C_7H_6Cl_4$: Calculated: C, 36.24%, H, 2.61%; Cl, 61.15%. Found: C, 35.20%; H, 2.60%; Cl, 61.70%.

EXAMPLE 14

Tetrachlorodimethylcyclopentadienes 1,2,3,4,5-pentachloro-5-methylcyclopentadiene (252.4 g., 1.0 mole) was placed in the 3 neck flask described in Example 1 and, after being heated to 50°C., trimethyl phosphite (145.0 g., 1.17 mole) was added slowly from the dropping funnel at such a rate as to maintain the temperature of the exothermic reaction close to 50°C. After the addition of the phosphite was completed (in 1.5 hour) the clear, brown solution was heated for 3 more hours between 50° and 53°C. Hydrolysis of the reaction mixture and subsequent steam distillation yielded a mixture of 1,2,3,4-tetrachloro-5,5-dimethylcyclopentadiene, 2,3,4,5-tetrachloro-1,5-dimethylcyclopentadiene, 1,3,4,5-tetrachloro-2,5-dimethylcyclopentadiene in 94% yield (218.0 g., 0.94 mole) in form of a pale yellow oil, b.p. 40° to 47°C. at 9.42 mm., $n_D^{25}$ 1.5287–1.5321.

Analysis for $C_7H_6Cl_4$: Calculated: C, 36.24%; H, 2.61%; Cl, 61.15%. Found: C, 36.24%; H. 2.83%; Cl, 61.17%.

Infrared spectrum of the reaction product indicated the presence of all three isomeric dimethyltetrachlorocyclopentadienes. Fractionation through a good column separated the mixture into pure components, each of which had a characteristic infrared spectrum.

EXAMPLE 15

1,2,3,4,5-pentabromo-5-methylcyclopentadiene

The substitution of trimethyl phosphite (136.5 g., 1.1 mole) for triethyl phosphite, of hexebromocyclopentadiene (539.6 g., 1.0 mole) for hexachlorocyclopentadiene and of hexane (2.5 l.) for petroleum ether in Example 1 and raising the reaction temperature to 30°C. resulted in the formation of 1,2,3,4,5-pentabromo-5-methylcyclopentadiene in better than 90% yield; $n_D^{25}$ 1.6618, melting point 60°–61°C.

Analysis for $C_6H_3Br_5$: Calculated: C, 15.18%; H, 0.64%; Br, 84.18%. Found: C, 14.67%; H, 1.09%; Br, 84.54%.

When fractionation instead of hydrolysis was used in the workup of the reaction products a substantial yield of methyl phosphorobromidate, $Br(CH_3O)_2PO$, b.p. 54°–57°C. at 0.7–0.9 mm., $n_D^{25}$ 1.4462 was obtained as a second product.

The use of the compounds of the present invention as intermediates for the preparation of insecticides having low mammalian toxicity is illustrated by the following examples:

EXAMPLE 16

A mixture 2 mole proportions of 5-methylpentachlorocyclopentadiene and 3 mole proportions of bicyclo (2,2,1)hepta-2,5-diene was charged to a closed reaction vessel provided with thermometer and a reflux condenser. The reaction mixture was refluxed at the initial temperature of 106.5°C. The pale yellow mixture gradually darkened and the reflux temperature increased to 141°C. in about 23 hours. A vacuum was applied and the excess of bicyclo(2,2,1)hepta-2,5-diene was distilled, removed by distillation. The residue was then fractionated and the Diels-Alder adduct was recovered at 117°–120°C. at 0.22 mm. which solidified upon cooling. The product was then recrystallized from n-hexane as white crystals (m.p. 96°–98°C.). This was identified as:

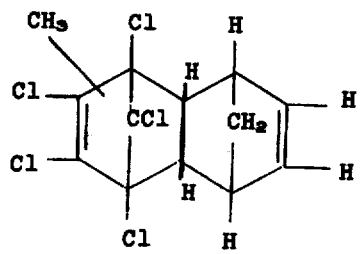

This product had insecticide activity providing 100% kill of mosquito larvae at 0.1 ppm, and on red flour beetle at 0.5% concentration.

EXAMPLE 17

The procedure of Example A above was repeated except that pentachloro-5-ethylcyclopentadiene was used in place of pentachloro-5-methylcyclopentadiene. The product 1,2,3,4,10-pentachloro-10-ethyl-1,4,4a,5,8,8a-hexahydro-1,4,5,8-dimethanonaphthalene (b.p. 107°C. at 0.06 mm. $n_D^{25}$ 1.5628) was identified as a compound of the structure:

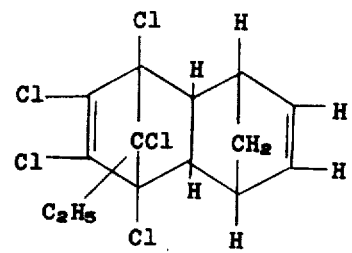

This compound had insecticide activity providing 90% kill of mosquito larvae at 1.3 ppm., 90% kill flour beetle at 0.5% concentration and 100% kill curculio at 0.1% concentration.

The mammalian toxicity of this compound $LD_{50}$(mgm/kg) was more than 794 but less than 1260 as compared to an $LD_{50}$ $_{50}$(mgm/kg) of 81.5 for the related compound in which the ethyl group is replaced by a chlorine atom.

It will be observed in the compounds of Examples 16 and 17 that the alkyl substituent is on the bridge carbon atom of the norborene ring. This occurs because the halogenated cyclopentadiene intermediates of this invention have the alkyl or other R group on the saturated carbon, i.e., at position 5 of the ring. This is in contrast to halogenated cyclopentadienes of the prior art wherein the 5 position is fully halogenated and R groups when present are elsewhere on the ring. When such compounds are employed as intermediates to produce insecticides as illustrated in Examples 17 and 18, it is not possible to place the organic R group on the bridge carbon atom. As shown, the presence of an organic R group substituent on the bridge carbon atom greatly reduces mammalian toxicity without serious reduction in toxicity to lower forms of animal life.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

I claim:

1. Compound of the formula

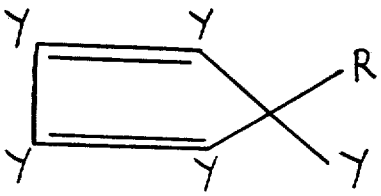

wherein Y is a halogen of atomic weight between 35 and 80; R is alkoxyalkyl having at least 2 and a maximum of 6 carbon atoms.

2. A compound in accordance with claim 1 in which R is 2-methoxyethyl.

3. A compound in accordance with claim 2 which is 1,2,3,4,5-pentachloro-5-(2-methoxy ethyl) cyclopentadiene.

* * * * *